United States Patent [19]

Laure

[11] 4,059,854
[45] Nov. 29, 1977

[54] RIBBED FINGER JOINT IMPLANT

[75] Inventor: George R. Laure, Kalamazoo, Mich.

[73] Assignee: Laure Prosthetics, Inc., Portage, Mich.

[21] Appl. No.: 756,240

[22] Filed: Jan. 3, 1977

[51] Int. Cl.² .............................................. A61F 1/24
[52] U.S. Cl. .................................... 3/1.91; 128/92 C
[58] Field of Search ........................ 3/1.9, 1.91–1.913, 3/1; 128/92 C, 92 CA

[56] References Cited

U.S. PATENT DOCUMENTS

| | | | |
|---|---|---|---|
| 2,719,522 | 10/1955 | Hudack | 128/92 CA |
| 3,506,982 | 4/1970 | Steffee | 3/1.91 |
| 4,011,603 | 3/1977 | Steffee | 3/1.91 |

Primary Examiner—Ronald L. Frinks
Attorney, Agent, or Firm—Blanchard, Flynn, Thiel, Boutell & Tanis

[57] ABSTRACT

An endoprosthetic joint formed by head and socket members which are adapted to be implanted in a thumb or a finger and can be suitably snapped together. The socket member is provided with structure exteriorly thereof, such as a pair of outwardly projecting webs disposed on diametrically opposite sides thereof, for permitting the muscles, ligaments and tendons to be sutured to these webs to thereby positionally relate same to the implanted joint, whereby proper balancing in the tensions imposed on the muscles and tendons is achieved during pivoting of the digit.

2 Claims, 4 Drawing Figures

RIBBED FINGER JOINT IMPLANT

FIELD OF THE INVENTION

This invention relates to an endoprosthetic joint which can be implanted into the digit of a subject human or animal and which will closely approximate the appearance and motion of a healthy natural joint.

BACKGROUND OF THE INVENTION

The subject of endoprosthetic joints has received a great deal of attention over the past several years and has particularly received much attention in recent years due in part to the availability of improved materials inert to human or animal bodies and to improved techniques for manipulating same. However, in spite of such intensive study, the endoprosthetic joints previously available, while in many cases satisfactory to a limited degree, are far from fully satisfactory and intensive work is continuing for the further improvement of such endoprostheses.

One particular area which has been extensively studied relates to the endoprosthetic joints used to replace the digital (i.e. finger and thumb) joints. While many such prosthetic joints have been developed for this purpose, and while many of these joints have been observed to perform with varying degrees of success, nevertheless one common problem encountered with most endoprosthetic joints relates to the inability to successfully hold the ligaments and tendons of the digit in proper position around the joint. A finger has what is commonly called the "volar plate." This plate, which includes the tendons and ligaments of the finger, forms a layer positioned adjacent the bottom of the joint. When the natural joint is replaced by an endoprosthetic joint, this volar plate is no longer attached to the joint and is thus not secured in its normal position. This volar plate thus has a tendency to become displaced, as by sliding sidewardly with respect to the joint, which in turn seriously affects both the appearance and the desired natural manipulation of the finger. This displacement of the volar plate causes an imbalance in the tendons as the finger is flexed, whereby proper pivoting movement of the finger and the return thereof into a straight position is seriously affected.

Accordingly, it is an object of the present invention to provide an improved endoprosthesis for a digital joint, and particularly a finger, including knuckle, joint, which can successfully overcome the above-mentioned problem so that a digit having the endoprosthetic joint implanted therein will have a natural appearance and be capable of natural movement.

More specifically, it is an object of this invention to provide an improved endoprosthetic joint, as aforesaid, which is particularly suitable for the finger joint between the phalangeal and metacarpal bones and includes head and socket members which can be easily implanted into the bone structure on either side of the joint, with the head and socket members being suitably snapped together. The endoprosthetic joint of this invention is provided with suitable structure associated with the socket member, such as external webs, which permit the ligaments, muscles and/or tendons to be sutured to the implanted joint substantially on diametrically opposite sides thereof so that they are maintained in the desired position. This thus permits a natural pivotal movement of the digit while at the same time maintaining a proper balance on the muscles, tendons and ligaments.

Figure 1:
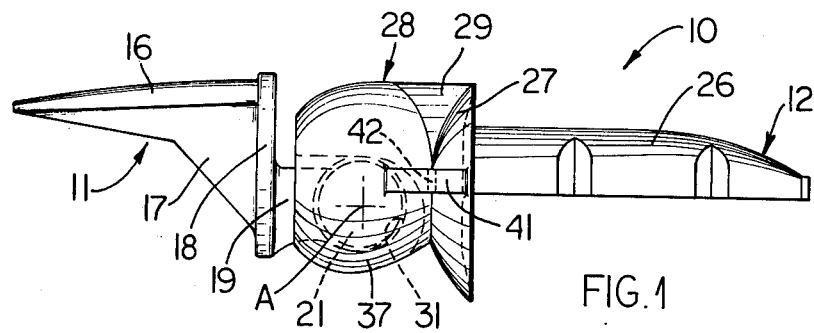
FIG. 1 is a side elevational view of an endoprosthetic joint embodying the invention.

Certain terminology will be used in the following description for convenience in reference only and will not be limiting. For example, the words "upwardly," "downwardly," "leftwardly" and "rightwardly" will refer to directions in the drawings to which reference is made. The word "inwardly" will refer to directions toward the center of the joint and designated parts thereof, and will have specific reference to relative movement between the socket and head members in a direction toward one another for causing same to be snapped together. Said terminology will include the words specifically mentioned, derivatives thereof and words of similar import.

SUMMARY OF THE INVENTION

The objects and purposes of the present invention, as briefly outlined above, are met by providing an endoprosthetic joint formed by head and socket members which are adapted to be implanted in a digit and can be suitably snapped together. The socket member is provided with structure exteriorly thereof, such as a pair of outwardly projecting webs disposed on diametrically opposite sides thereof, for permitting the muscles, ligaments and tendons to be sutured to these webs to thereby positionally relate same to the implanted joint, whereby proper balancing in the tensions imposed on the muscles and tendons is achieved during pivoting of the digit.

DETAILED DESCRIPTION

Referring to the drawings, there is shown an endoprosthetic joint 10 for the replacement of a digital joint in a human hand. The joint 10, which comprises a headed member 11 cooperating with a socket member 12, is designed specifically as a replacement for the joint between the phalangeal and metacarpal bones (i.e. a metacarpal-phalangeal joint), although the endoprosthetic joint constructed in accordance with the present invention is obviously applicable to other digital joints.

Figure 2:
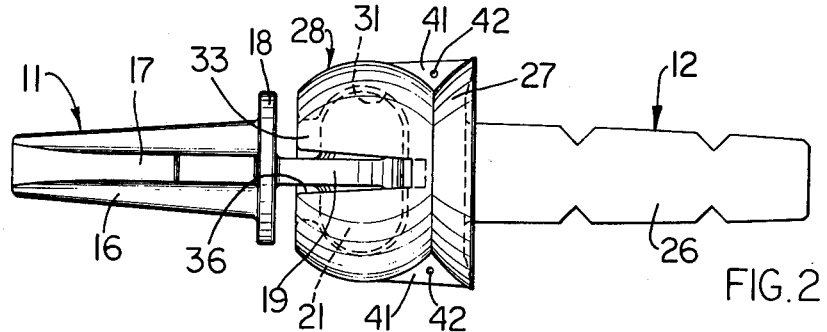
FIG. 2 is a bottom view of the joint shown in FIG. 1.
Figure 3:
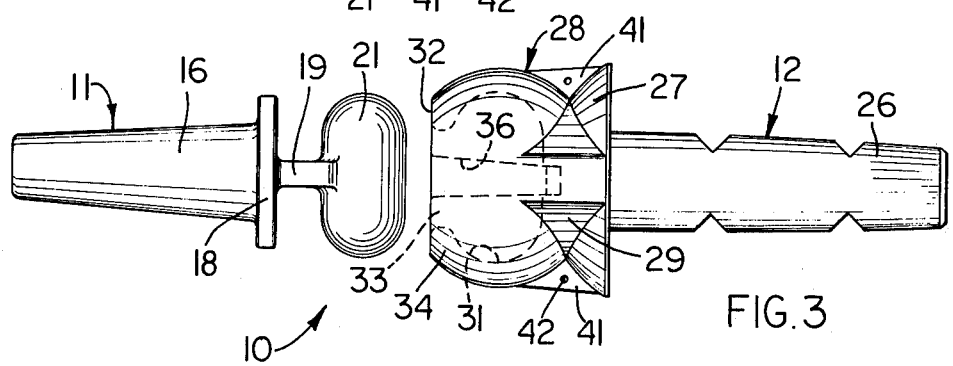
FIG. 3 is a top view of the joint of FIG. 1 but with the parts in a separated condition.
Figure 4:
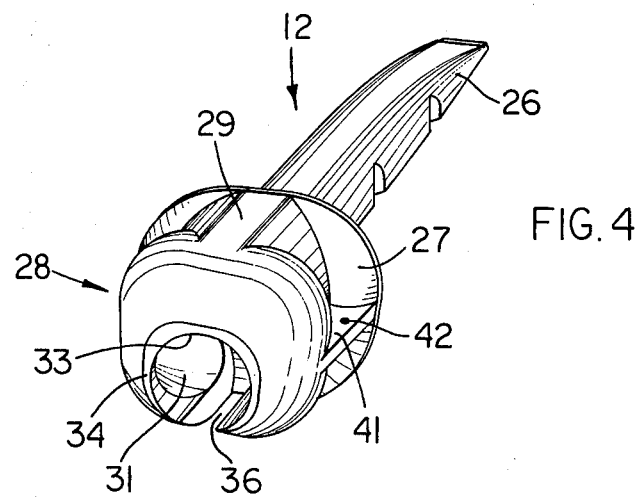
FIG. 4 is a perspective view of the socket member.

The headed member 11 includes a stem 16 provided with a reinforcing or rigidifying flange 17 projecting downwardly from the lower surface thereof. The stem is of a generally tapered configuration, as illustrated in FIGS. 2 and 3, so as to be narrowest at its free end. The other end of the stem terminates in a platelike anchor portion 18 which extends downwardly from the stem 16. A neck portion 19 protrudes from the other side of the anchor portion 18 adjacent the lower part thereof, which neck portion 19 is of a platelike structure and is positioned substantially midway between the opposite sides of the anchor portion 18. The neck portion 19 terminates in an enlarged head 21 which, in the illustrated embodiment, is of an elongated spheroid shape. The head 21 is secured to the neck portion 19 in spaced relation from the anchor portion 18. The head portion 21 is also spaced downwardly in its entirety from the stem 16.

Considering now the socket member 12, same includes an elongated stem 26 which is fixed to and projects outwardly from a cup-shaped guard 27. This guard is in turn fixedly connected to an enlarged socket portion 28 which is of a generally spherical configuration. The partially spherical external surfaces of the guard 27 and socket portion 28 are joined, in the upper regions thereof, by a bridging portion 29 which extends between the guard 27 and socket portion 28 for rigidifying same.

Socket portion 28 is provided with a generally spheroid cavity 31 which is shaped similar to but slightly larger than the head 21 so as to hingedly accommodate same therein. The front of the socket portion 28 is provided with a somewhat flattened wall 32 in which there is provided an aperture 33 for permitting insertion of the head 21 into the socket cavity 31. The aperture 33 is surrounded by a flexible lip portion 34 which is sufficiently deformable so as to permit insertion of the head 21 into the socket 31. The socket portion 28 is additionally provided with a narrow elongated slot 36 which communicates with the lower part of the aperture 33 and extends downwardly so as to open through the bottom wall 37 of the socket portion. The socket cavity 31 is, as shown in FIG. 1, positioned in the lower part of the socket portion 28 so that the hinge axis A as defined when the head 21 is positioned within the socket cavity 31 is thus disposed below the center of the socket portion 28, and is also disposed below the stems 16 and 26.

The structure of the endoprosthetic joint 10 as described above is somewhat conventional and, in fact, is similar to the construction of the joint disclosed in U.S. Pat. No. 3,506,982.

According to the present invention, the endoprosthetic joint 10 is provided with structure which enables the tendons, ligaments and muscles associated with the digit to be fixedly anchored to the implanted joint. This is accomplished in the present invention by providing the socket member 12 with anchoring or attachment structure formed as webs or ribs 41 which are positioned exteriorly of the socket member and are associated with the socket portion 28. These ribs 41 are, in the illustrated embodiment, integrally molded with the socket member and are positioned in the region of and extend between the exterior spherical surfaces formed on the guard 27 and socket portion 28. In the illustrated embodiment, the socket member 12 is provided with two ribs 41 positioned on opposite sides of the socket portion 28 and disposed substantially within a diametrical plane. These ribs 41 are approximately aligned with the under surface of the stem 26 but, as is evident from FIG. 1, are positioned above the hinge axis A. The ribs 41, by being positioned in the region between the curved exterior surfaces of the guard 27 and socket portion 28, thus do not project outwardly beyond the dimensional limits defined by either the guard 27 or the socket portion 28, whereby they do not interfere with the implanting of the joint in a digit.

Each of the ribs 41 is preferably provided with one or more small openings 42 extending therethrough, which openings permit the ligaments, tendons or muscles to be sutured to the ribs 41 during the implant procedure.

In use, for example when the joint 10 is being used to replace a natural digital joint, such as a metacarpal-phalangeal joint, the stems 16 and 26 are inserted into the bones in a manner already known, with the stem 16 being inserted into the phalangeal bone and the stem 26 being inserted into the metacarpal bone. The two members 11 and 12 are then suitably snapped together by inserting the head 21 into the socket cavity 31, which insertion is permitted by the resilient lip 34. When thus joined together, the finger is accordingly permitted to undergo a natural movement as accommodated by the pivoting movement of the headed member 11 relative to the socket member 12. The operation of the joint is, in this respect, well known.

During the surgical implant of the joint, the muscles, tendons and/or ligaments are suitably sutured to the socket portion 28, specifically be being sutured to the ribs 41 by inserting the suture through the openings 42. This thus anchors the tissues relative to the socket portion 28 so that they are properly positioned and will remain in this position so that the digit will have a controlled movement similar to a natural healthy joint.

Since the center of rotation between the head 21 and socket 31 is positioned substantially below the central plane of the stems 16 and 26, this thus permits a more natural positioning of the tendons and muscles with respect to the prosthesis structure and a more naturally operating joint.

While a variety of materials are available which are effective for this purpose, they must in all cases be materials which are inert to the body, stiff enough to provide the necessary mechanical strength and capable of providing an easily operated hinge action. In the present embodiment, the headed member 11 is made from a chromium cobalt alloy identified by the generic trade designation of ASTM F-75. The socket portion 12 is preferably made of any of several plastics materials having sufficient self-lubricating properties as to make them readily movable with respect to the head portion, such as any of several high density polyethylene materials.

The joint 10 as described above, and as illustrated in the drawings, is designed specifically for replacing the natural metacarpal-phalangeal finger joint. For this reason, the joint 10 is designed to not only allow for the natural pivoting movement of the finger, as permitted by the relative swinging between the socket and headed members about the axis A, but is also designed to permit at least limited sideward displacement of the headed member with respect to the socket to thereby closely approximate the permissible movements of the natural joint. The head 21 is thus of an elongated spheroid shape and the slot 36, which receives therein the neck portion 19, is tapered and of a width somewhat greater than that of the neck portion, whereby the joint permits limited sideward pivoting of the finger.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property or privilege is claimed are defined as follows:

1. In an implantable-type endoprosthesis for a digital joint, the endoprosthesis including a protuberant headed member provided with a stem portion at one end thereof for affixing said member in a bone and a protuberant head portion at the other end thereof, and a socketed member provided with a stem portion at one end thereof for fixing said member in a bone and a socket portion at the other end thereof which defines an interior socket cavity in which the protuberant head portion is removably retained and swingably supported, said socket portion including a socket part having a generally spheroid external configuration, said socket portion also including an annular guard flange fixedly connected to the rearward side of said socket part so as to be interposed between said socket part and the respective stem portion, said guard flange and said socket part having opposed external surfaces which diverge away from one another, comprising the improvement wherein said socket portion has means fixedly associated therewith and disposed exteriorly thereof for permitting the ligaments, muscles or tendons to be fixedly tied thereto, said means defining a pair of ribs which are integral with said socket portion and extend between the diverging external surfaces of said socket part and said guard flange, said ribs extending in a direction approximately parallel to the elongated direction of the respective stem portion and being disposed in wide circumferentially spaced relationship with respect to the socket part so as to be positioned on opposite sides of the joint when implanted in a digit, said ribs having opening means extending therethrough for permitting suturing of the tendons, ligaments or muscles thereto, and said ribs being dimensioned so as to not project outwardly beyond the outer dimensional limits defined by either said guard flange or said socket part so as to not interfere with the implanting of the joint in a digit.

2. A joint according to claim 1, wherein the pair of ribs are substantially parallel and project outwardly from substantially diametrically opposite sides of the socket part, wherein said protuberant head portion and said socket cavity are shaped to permit relative pivoting movement between said socketed and headed members primarily within a single plane about a pivot axis which extends longitudinally of the protuberant head, said pivot axis extending substantially perpendicular to the longitudinally extending directions of said stem portions but being disposed substantially below the central longitudinal planes of said stem portions, and said ribs being positioned above said pivot axis in approximate alignment with the stem portion associated with said socketed member.

* * * * *